United States Patent [19]

Bhogal et al.

[11] Patent Number: 6,113,916

[45] Date of Patent: *Sep. 5, 2000

[54] METHOD OF ENHANCING CELL MEDIATED IMMUNE RESPONSES

[75] Inventors: Balbir S. Bhogal, Wood Lands, Tex.; Krishnaswamy I. Dayalu; Jay D. Gerber, both of Lincoln, Nebr.

[73] Assignee: American Cyanamid Company, Madison, N.J.

[ * ] Notice: This patent is subject to a terminal disclaimer.

[21] Appl. No.: 08/406,958

[22] PCT Filed: Sep. 21, 1993

[86] PCT No.: PCT/US93/08900

§ 371 Date: May 25, 1995

§ 102(e) Date: May 25, 1995

[87] PCT Pub. No.: WO94/07531

PCT Pub. Date: Apr. 14, 1994

Related U.S. Application Data

[63] Continuation of application No. 07/952,248, Sep. 28, 1992, abandoned, which is a continuation-in-part of application No. 07/634,237, Dec. 26, 1990, abandoned, which is a continuation-in-part of application No. 07/575,921, Aug. 31, 1990, abandoned, which is a continuation-in-part of application No. 07/530,669, May 29, 1990, abandoned.

[51] Int. Cl.$^7$ .................................................. A61K 39/00
[52] U.S. Cl. .................................... 424/264.1; 424/184.1; 424/825
[58] Field of Search ...................... 424/264.1, 184.1, 424/825

[56] References Cited

U.S. PATENT DOCUMENTS

| 4,341,763 | 7/1982 | Zygraich | 424/215.1 |
| 4,894,332 | 1/1990 | Schaller et al. | 435/69.3 |
| 4,981,684 | 1/1991 | Mackenzie et al. | 424/193.1 |
| 4,985,243 | 1/1991 | Faulds et al. | 424/164.1 |

FOREIGN PATENT DOCUMENTS 9203157  3/1992  WIPO .

OTHER PUBLICATIONS

Ross et al (1984) Am. J. Ver. Res. 45(10):1899–1905.
Durisic et al. (1975) Acta Veterinaria (Beograd) 25(4):189–194.
Oboegbulem et al (1975) J. Nig. Vet. Med. Ass. 4(2):53–58.
Goodwin et al (1969) J. Hyg. Camb. 67:465–675.

*Primary Examiner*—Ponnathapura Achutamurthy

[57] ABSTRACT

This intention provides a method for enhancing a cell mediates immune response to *Mycoplasma hypneumoniae* in a newborn swine which involves administering a vaccine containing an effective amount of a protective antibody-inducing antigen to a pregnant sow, following by administering the vaccine to the newborn swine.

6 Claims, No Drawings

METHOD OF ENHANCING CELL MEDIATED IMMUNE RESPONSES

CROSS-REFERENCE TO RELATED APPLICATION

This is a National Stage Application of International Application No. PCT/US93/08900, International filing date Sep. 21, 1993, is a continuation in the United States of U.S. Ser. No. 07/952,248, filed Sep. 28, 1992, now abandoned, which is a continuation-in-part of U.S. Ser. No. 07/634,237, filed Dec. 26, 1990, now abandoned, which is a continuation-in-part of U.S. Ser. No. 07/575,921, filed Aug. 31, 1990, now abandoned, which is a continuation-in-part of U.S. Ser. No. 07/530,669, filed May 29, 1990, now abandoned, the contents of which are hereby incorporated by reference.

FIELD OF THE INVENTION

The invention relates generally to the field of vaccines, and more specifically, to methods of enhancing cell mediated immune responses in newborn piglets to *Mycoplasma hyopneumoniae* antigens.

BACKGROUND OF THE INVENTION

There have been documented instances in the art of passively immunizing neonates against infection with a selected disease-causing agent by administering a vaccine to a pregnant animal or to a nursing mother. These passive immune responses are believed to be due to the transfer of maternal IgA antibodies through the placenta to the infant and/or by intestinal absorption of maternal immunoglobulins present in the colostrum or milk by the neonate.

Colostrum and milk, which provide protective immune factors to the neonate, also have an extraordinary and unique combination of carbohydrates, fats, amino acids, minerals, vitamins, growth promoting factors such as epidermal-growth factor, insulin, and somatomedins, as well as lactoferrin, interleukin-1 (IL-1) and vasoactive intestinal peptides and some neuropeptides.

After ingestion of colostrum, maternal immune factor, especially antibodies, antibody producing cells, and T cells are seeded via intestinal mucosal tissue and maintained in various lymphoid tissues of the neonate during the early post-natal period of maturation of its immune system until the infant's own lymphoid system is capable of antibody production and induction or priming of T cells. Human colostrum and milk contain activated and memory T lymphocytes up to 73% of the total lymphocyte population. Memory T lymphocytes make up to 92% of the total lymphocyte population. Furthermore, experimental data on human colostrum and milk suggest that virtually all (99.8%) of T cells of the helper phenotype ($CD^{4+}$), and most (92%) of the T cells of cytotoxic/suppressor phenotype ($CD^{8+}$) are memory T cells. These T lymphocytes, in collaboration with other immune factors, play an important role in the immunological development of the neonate with respect to its ability to respond to future encounters with environmental antigens or deliberate exposure via vaccinations.

In the art of immunology it is well established that exposure of neonatal animals to a majority of environmental antigens or vaccination usually results in tolerance induction depending on various factors, such as type of antigen, dose and route of administration and genetic background. In contrast, a similar exposure of the adults would invariably result in an immune response.

The cellular basis of this disparate responsiveness of neonates and adults is not clearly defined. This phenomenon may be attributed to two critical factors, namely, status of maternal immune reactivity and maternal B and T cell repertoire, and the post-natal antigen exposure of the neonate by gram negative microbes (LPS). For example, colonization of the gut occurs rapidly after birth, e.g., in calves about 4 days, and in pigs about 1 week.

There exists a need in the vaccine art for a method of enhancing immunity, particularly non-antibody mediated immunity (or cell mediated immunity), in neonates lacking fully developed immune systems.

SUMMARY OF THE INVENTION

The present invention provides a method for enhancing cell mediated immune responses of newborn animals, particularly swine, to a Mycoplasma antigen or immunogenic agent, specifically an *M. hyopneumoniae* antigen. This method involves vaccinating pregnant animals with a vaccine containing the selected immunogenic agent and then administering a vaccine containing the same immunogen to the resulting newborns.

Other aspects and advantages of the present invention are described further in the following detailed description of the preferred embodiments thereof.

DETAILED DESCRIPTION OF THE INVENTION

The present invention provides a method of enhancing cell mediated immune responses of newborn animals, particularly swine, to a selected Mycoplasma immunogen or antigen. This method involves administering to a pregnant sow a vaccine composition containing a selected Mycoplasma immunogenic agent and subsequently administering a suitable dose of the vaccine composition containing the same immunogen to the newborn piglet(s) to achieve a cell mediated immune response to that immunogen in the piglet.

This method elicits an enhanced cell mediated immune (CMI) response in the nursing and vaccinated newborns to the specific immunogen upon the second presentation of the immunogen through at least one direct vaccination of the piglet. Additionally, where a neonate is immunodeficient, the method of the invention, particularly via more than one vaccination of the nursing piglets, permits the maternal immune repertoire to be reconstituted in the newborn.

As used herein, the terms Mycoplasma immunogen, immunogenic agent or antigen may refer to a whole Mycoplasma pathogen, preferably inactivated. These terms also include a pathogen protein isolated in crude form and/or purified therefrom or a synthetic protein, as well as some fragment of the synthetic, purified or isolated pathogenic protein having antigenic properties. It is possible that the antigen may also include a non-protein biological material from said pathogen.

By "enhanced CMI response" is meant a CMI response in the piglet comprising the production of T cells protective against the infectious agent bearing the antigen, which response is greater than that observed in pregnant sows induced by administration of the vaccine, or that observed when the vaccine is directly administered to a piglet only or that observed in unvaccinated piglets born to vaccinated sows. By "newborn" is meant a recently-born animal of less than about 10 weeks of age. Preferably in the method of this invention, the newborn has nursed on maternal colostrum after birth. Preferably, the newborn has nursed on maternal colostrum within the first 48 hours after birth. By "effective amount" or "effective immunogenic amount" as used herein is meant the amount of antigen which is capable of inducing in the vaccinated animal a protective cell-mediated immune response, and optionally, a protective antibody response. Alternatively, the effective amount may be defined as that required to prevent or lessen the severity, for some period of time, of any one of the disorders which result from infection with M. hyopneumoniae.

Thus, as one example, the present invention provides a method of enhancing cell mediated responses of piglets against a selected infectious agent, M. hyopneumoniae. The method involves administering a vaccine containing an effective amount of an antigen or immunogen from the infectious agent to a sow prior to birth of its piglets. According to the method of this invention, this vaccine can be administered to the sow prior to breeding. However, the vaccine is preferably administered to a pregnant sow between about 6 weeks and 2 weeks prior to farrowing, i.e., giving birth.

After birth, the piglets nurse on the milk and colostrum from the vaccinated mother, preferably within the first 48 hours after birth. It is preferred that the piglets nurse from the mother for a longer period of time. The piglet(s) then receive a primary vaccination, i.e., an appropriate first dose of the same vaccine composition that was administered to the mother. This primary vaccination is administered to the piglets at between 3 days and 3 weeks after birth. Preferably the primary vaccination is administered to the piglet one week from birth.

Optionally, where desired, the vaccine is then administered to a piglet a second time, i.e., a secondary vaccination, approximately two weeks after the primary vaccination. The secondary vaccination can be desirable when the piglet is determined to be immunodeficient or when it has nursed insufficiently on material colostrum.

The immunoregulatory effect provided by the method of this invention is achieved even if the piglets are weaned after 48 hours. In the studies described below, the specific proliferative responses of T lymphocytes, that is, the cell mediated immune response, from piglets born to and nursed by sows vaccinated with the Mycoplasma hyopneumoniae vaccine were ten to twenty fold higher after the primary vaccination of the piglets than the responses of T lymphocytes from piglets born to, and nursed by non-vaccinated sows after primary vaccination of these piglets.

While not wishing to be bound by the theory of the mechanism by which this method works, the inventors currently believe that colostrum of the previously vaccinated sows contain specific B cells and T cells carrying internal image antibodies to the antigen. The lymphoid organs of piglets nursing within at least the first 48 hours after birth on this colostrum are seeded with these maternal B and T cells.

Such lymphocytes colonize and proliferate in the piglet's lymphoid tissues and determine subsequent immunoreactivity of the piglet to the vaccine antigen. Upon exposure to the vaccine after birth, e.g., the primary vaccination, the piglet's immune system mounts an enhanced cell-mediated immune response to the immunogen in the vaccine.

In the course of a given immune response antibodies called idiotypes (Id or Ab-1), which have several immunogenic determinants formed by the interactions or folding of the hypervariable chains of Ab-1, are produced to a given antigen, in this case, the M. hyopneumoniae antigen. A second generation of immune responses, i.e., the generation of antibodies to the immunogenic determinants of Ab-1, also occurs as a part of the normal immunoregulatory circuits during the normal immune response. The antibodies generated to the Id determinants of Ab-1 during the course of an immune response to a given antigen are called anti-idiotypes (anti-Id or Ab-2). Several sets of Ab-2 antibodies, such as Ab-2$\beta$, Ab-2$\tau$, and Ab-2$\alpha$, can be produced against different idiotypic determinants of Ab-1. Some of the Ab-2, in particular Ab-2$\beta$ produced against the Id located within the antigen binding site of Ab-1 antibodies, can bear a structural conformity to the antigen recognized by Ab-1. These Ab-2 antibodies can represent a mirror image or surrogate antigen to the host's immune system by virtue of their conformation, even though chemically they are proteins and not lipopolysaccharide (LPS) or LPS-like antigens. This forms the basis of idiotypic mimicry or internal imaging of a given antigen and provides a logical extension of the immune networks theory of Jerne, Ann. Immunol., 125(c):373 (1974)].

This system has a potential application in modulating immune responses, and may be useful in modulating the immunoresponsiveness of newborns. The immunization of pregnant animals induces a B cell response, e.g., immunoglobulin Ab-1, and a T cell response, such as T helper cells characterized by specificity for a given antigen. Studies in the murine system suggest that Lyb5$^-$ B lymphocytes and Lyb5$^-$-like B lymphocytes, even though they are prone to tolerance induction by LPS-like antigens, can be very effectively stimulated for a positive and productive immune response by mirror-image surrogate antigens such as those represented by anti-idiotypic (Anti-Id) antibodies. In addition, Anti-Id has also been shown to enhance development of Lyb5$^+$ B subset of lymphocytes. Therefore the most practical natural means by which: (1) tolerization of Lyb5$^-$ B lymphocytes and Lyb5$^-$-like B lymphocytes can be prevented and (2) development of Lyb5$^+$ B lymphocytes$^-$ can be enhanced in the newborn is via maternal vaccination and priming of the Lyb5$^-$ subset of B cells with Anti-Id. In this way, the newborn's lymphoid organs are seeded with these cells via ingestion of colostrum before exposure of the newborn to environmental antigens.

As exemplified herein, immunization of pregnant sows (or sows prior to breeding) with a given antigen of a selected infectious agent, e.g., M. hyopneumoniae, induces Ab-1 antibodies which are specific for the epitopes on that pathogen. Ab-2 antibodies are also produced against the Id of Ab-1. Some of these Ab-2 or Anti-Id bear structural conformity to the Mycoplasma antigens or a particular epitope of that antigen. Both the Ab-1 and Ab-2 maternal antibodies are carried to the newborn by antibody producing lymphocytes (B lymphocytes) during ingestion of colostrum in the first few hours after birth. Sow colostrum contains as much as 30% lymphocytes w/v for the first 16 hours postpartum. B and T lymphocytes absorbed through the intestinal mucosa in the first few hours of the newborn's life destines the establishment of the future T and B cell repertoire in various lymphoid organs.

This process is controlled by several factors including the specificity of the lymphocyte repertoire of the colostrum (which reflect the immune reactivity and repertoire of the mother), immaturity of the newborn's own B cell repertoire, and exposure of the newborn to environmental or selected vaccine antigens.

Vaccine compositions useful in the method of the invention may be prepared as pharmaceutical compositions containing an effective immunogenic amount of the selected immunogen, e.g., the inactivated M. hyopneumoniae virus described below, as an active ingredient in a nontoxic and sterile pharmaceutically acceptable carrier. Such an acceptable carrier may be readily selected by one of skill in the art, and is preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well known sterilization techniques.

Such vaccine compositions useful in this method may comprise the inactivated vaccine component described above or other Mycoplasma immunogens from the same or different Mycoplasma species. Still other antigens suitable for administration to swine, which are not of Mycoplasma origin, may be included in the vaccine composition administered according to this method.

These antigens may be mixed with optional pharmaceutically acceptable auxiliary substances as required to approximate physiological conditions such as pH adjusting and buffering agents, preservatives, emulsifiers and the like. Alternatively or additionally, the inactivated M. hyopneumoniae may be admixed or adsorbed with a conventional adjuvant, e.g., Amphigen, mineral oil and lecithin, aluminum hydroxide, muramyl dipeptide, and saponins such as Quil A.

A preferred embodiment of the vaccine composition which may be administered according to the method of the invention contains an aqueous suspension or solution containing the inactivated P-5722-3 strain of M. hyopneumoniae. M. hyopneumoniae strain P-5722-3 was deposited with the American Type Culture Collection, 12301 Parklawn Dr., Rockville, Md., under Accession No. 55052.

The vaccine containing this strain is available commercially under the tradename RespiSure [SmithKline Beecham] and is the subject of pending U.S. Ser. No. 08/306,636, filed Sep. 15, 1994, which is a continuation of Ser. No. 07/917,922, filed Aug. 21, 1992, now abandoned, which is a continuation of U.S. Ser. No. 07/634,237, filed Dec. 26, 1990, now abandoned the contents of which are hereby incorporated by reference. The vaccine strain is preferably buffered at physiological pH, in a form ready for injection.

For purposes of this invention, a desirable immunogenic amount of inactivated M. hyopneumoniae virus for vaccination of the sow or the newborn, when administered as the sole active ingredient in a vaccine composition is between $5 \times 10^8$ CCU and $5 \times 10^9$ CCU. In a vaccine composition containing additional antigenic components, the same immunogenic amount or a reduced amount of M. hyopneumoniae may be employed. For use in the method of this invention, it is preferred that the vaccine composition is in unit dosage forms, containing preferably about 2 mls, each dose containing the desired titer.

Other appropriate therapeutically effective doses can be determined readily by those of skill in the art based on the above immunogenic amounts, the condition being treated and the physiological characteristics of the animal. In the presence of additional active agents, these unit dosages can be readily adjusted by those of skill in the art.

According to the method of this invention, a desirable dosage regimen involves administration of one or two doses of desired vaccine composition to the sow, either pregnant or prior to breeding, where the antigenic content of each fraction is desirably as stated above, and at least one dose to the newborn to obtain the enhanced CMI response of this method. Preferably, where two or more doses are administered to the pregnant animal, the doses are administered at least two weeks apart. In the case of the M. hyopneumoniae vaccine of this invention, for primary immunization of pregnant swine, two doses are recommended approximately four weeks apart with the last dose administered two weeks before farrowing. A booster dose is recommended prior to each subsequent farrowing, when the interval between vaccinations is more than six months. After the birth of the neonates, primary immunization should be initiated between approximately 3 days and 3 weeks of age, preferably, one week of age.

The mode of administration of the vaccines of the invention may be any suitable route which delivers the vaccine to the host. However, the vaccine is preferably administered by intramuscular injection. Other modes of administration may also be employed, where desired, such as subcutaneously, intradermally or intravenously.

The following example of the invention is illustrative only and not intended to be limiting.

EXAMPLE 1

Vaccine Trial

Eight white landrace pregnant sows were vaccinated intramuscularly at a period estimated to be between approximately two and 6 weeks prior to farrowing with the RespiSure vaccine composition [SmithKline Beecham] in a 2 mL dose. A control group of 8 pregnant sows was used, which animals were never vaccinated against M. hyopneumoniae. Newborn piglets at between one and three weeks of age which were nursing, or had nursed from the mother for at least 48 hours from birth, from both vaccinated and control groups were then administered a primary vaccination intramuscularly with the same dose of the same vaccine composition.

Flow cytometry was performed according to manufacturer's instructions [FACSTAR$^{PLUS}$ (Becton Dickinson, San Jose, Calif.)]. The flow cytometer, equipped with a single argon ion laser, was used for phenotypic analysis of lymphocytes obtained from the piglets at different time intervals after vaccination. Phenotypic analyses of lymphoid cells by flow cytometry using monoclonals specific for cluster of differentiation (CD) markers such as CD4 and CD8 were used to assess the effects of vaccination on piglets at one week of age and to assess the priming of T cells of the CD4 and CD8 phenotypes. Murine monoclonal antibodies, anti-CD4 and anti-CD8, specific for swine T cell markers were obtained from the ATCC. Anti-CD2 was obtained from Dr Joan Lunney [USDA Beltsville].

The following Table I summarizes the effects of primary vaccination on the T cell profiles in peripheral blood lymphocytes of piglets.

TABLE I

| Group | Intervention: of Piglets | % Positive Cells | |
|---|---|---|---|
| | | CD4 | CD8 |
| 1 | Controls | 29 | 46 |
| | | 31 | 24 |
| | | 35 | 50 |
| | | 32 | 61 |
| | Average: | 32 | 45 |
| 2 | Vaccinated born & nursed by vaccinated sows | 69 | 36 |
| | | 72 | 16 |
| | | 70 | 31 |
| | | 83 | 40 |
| | Average: | 74 | 22 |

TABLE I-continued

| Group | Intervention: of Piglets | % Positive Cells CD4 | CD8 |
|---|---|---|---|
| 3 | Vaccinated | 26 | 42 |
|   | Nursed by | 36 | 30 |
|   | Non-vaccinated | 40 | 56 |
|   | Sows | 29 | 67 |
|   | Average: | 33 | 48 |

Mycoplasma antigens used in this study were prepared from the vaccine strain of mycoplasma as described in U.S. Ser. No. 08/306,636, filed Sep. 15, 1994, which has been incorporated by reference herein.

The lymphoid tissues of the piglets were removed aseptically at necropsy. Single cell preparations were prepared in tissue culture media RPMI 1640 containing 10% fetal calf serum and Penstrep [Gibco]. Cells were seeded in 96 well plates and incubated with or without antigen and with or without mitogens, such as Concanavalin A (ConA), or T cell mitogens and lipopolysaccharide (LPS), or B cell mitogens. After 72 to 96 hours cells were labeled with $^3$H-thymidine, and incubated further for 18 to 24 hours. Cells were harvested on filter papers and incorporation of thymidine measured on beta-counter (scintillation counter; cpm). The degree of proliferation of cells is expressed as counts per minute.

At two weeks after a single vaccination, T lymphocytes from the spleen (mean cpm $31 \times 10^{-3}$), peripheral and bronchial lymph nodes (mean cpm $8.6 \times 10^{-3}$), and peripheral blood (mean cpm $21 \times 10^{-3}$) of the piglets showed very high proliferative responses to Mycoplasma antigens.

The following paragraphs illustrate the responses seen in bronchial lymph nodes (BLN), peripheral lymph nodes (PLN), spleen, and peripheral blood lymphocytes (PBLs) following primary and secondary immunization and following challenge.

A. Differences in in vitro proliferative responses of lymphoid cells from piglets born and nursed by vaccinated or non-vaccinated sows: 14 days after first or primary vaccination with the vaccine composition sold under the tradename RespiSure at one week of age.

TABLE II

| Source of lymphoid cells | Antigen | Mean cpm($^3$H-thymidine incorporation) Piglets born to and nursed by vaccinated sows | Piglets born to and nursed by non-vaccinated sows |
|---|---|---|---|
| Lymph nodes (BLN) | M.hyopn. | 8,800 | 2,100 |
| Lymph nodes (PLN) | " | 8,600 | 2,400 |
| Spleen | " | 31,800 | 3,700 |
| PBLs | " | 21,300 | 2,400 | n = 12–16 piglets

B. Differences in in vitro proliferative responses of lymphoid cells from piglets born and nursed by vaccinated or non-vaccinated sows: 7 days after second or secondary vaccination with the vaccine composition sold under the tradename RespiSure at three weeks of age.

TABLE III

| Source of lymphoid cells | Antigen | Mean cpm($^3$H-thymidine incorporation) Piglets born to and nursed by vaccinated sows | Piglets born to and nursed by non-vaccinated sows |
|---|---|---|---|
| Lymph nodes (BLN) | M.hyopn. | 9,300 | 3,400 |
| Lymph nodes (PLN) | " | 10,100 | 2,100 |
| Spleen | " | 19,700 | 4,800 |
| PBLs | " | 28,300 | 32,400 | n = 12–16 piglets

The high degree of responsiveness of T lymphocytes to the vaccine antigens is associated with the presence of various Mycoplasma-specific immunocompetent T cells, especially T helper cells, in the lymphoid organs of piglets born and nursed by vaccinated sows. Post-primary vaccination responses of T cells from piglets born to vaccinated sows were comparable to the responses typically expected from a second vaccination in a piglet. This finding suggests the presence of T helper cells with a history of prior exposure to Mycoplasma antigens or antigen-like molecules.

C. Differences in in vitro proliferative responses of lymphoid cells from piglets born and nursed by vaccinated or non-vaccinated sows: 10 days after second or secondary vaccination with the vaccine composition sold under the tradename RepiSure at three weeks of age.

TABLE IV

| Source of lymphoid cells | Antigen | Mean cpm($^3$H-thymidine incorporation) Piglets born to and nursed by vaccinated sows | Piglets born to and nursed by non-vaccinated sows |
|---|---|---|---|
| Lymph nodes (BLN) | M.hyopn. | 10,100 | 3,600 |
| Lymph nodes (PLN) | " | 14,700 | 3,100 |
| Spleen | " | 26,100 | 11,200 |
| PBLs | " | 26,300 | 37,400 | n = 12 to 16 piglets

The responsiveness of lymphoid cells from vaccinated pigs of vaccinated sows were assessed at 7 and 10 days after secondary vaccination as described above. only marginal increases were observed, suggesting that a second vaccination would be of particular benefit to piglets that do not ingest adequate amounts of immune colostrum/milk under field conditions. While these colostrum-limited pigs may be less responsive to first vaccination, they would be able to mount a protective CMI response to a second vaccination.

D. Differences in in vitro proliferative responses of lymphoid cells from piglets born and nursed by vaccinated or non-vaccinated sows: 4 days after challenge infection with 2 mL virulent *M. hyopneumoniae* administered intranasally 10 days after secondary vaccination with the vaccine composition sold under the tradename RepiSure at three weeks of age.

TABLE V

| Source of lymphoid cells | Antigen | Mean cpm($^3$H-thymidine incorporation) | |
|---|---|---|---|
| | | Piglets born to and nursed by vaccinated sows | Piglets born to and nursed by non-vaccinated sows |
| Lymph nodes (BLN) | M.hyopn. | 25,500 | 3,400 |
| Lymph nodes (PLN) | " | 5,700 | 3,000 |
| Spleen | " | 4,900 | 18,200 |
| PBLs | " | 4,700 | 2,400 | n = 12 to 16 piglets

E. Differences in in vitro proliferative responses of lymphoid cells from piglets born and nursed by vaccinated or non-vaccinated sows: 7 days after challenge infection with virulent *M. hyopneumoniae* given 10 days after secondary vaccination with the vaccine composition sold under the tradename RepiSure at three weeks of age.

TABLE VI

| Source of lymphoid cells | Antigen | Mean cpm($^3$H-thymidine incorporation) | |
|---|---|---|---|
| | | Piglets born to and nursed by vaccinated sows | Piglets born to and nursed by non-vaccinated sows |
| Lymph nodes (BLN) | M.hyopn. | 44,300 | 19,980 |
| Lymph nodes (PLN) | " | 5,200 | 2,600 |
| Spleen | " | 4,700 | 9,300 |
| PBLs | " | 4,100 | 2,200 | n = 12 to 16 piglets

F. Differences in in vitro proliferative responses of lymphoid cells from piglets born and nursed by vaccinated or non-vaccinated sows: 11 days after challenge infection with virulent *M. hyopneumoniae* given 10 days after secondary vaccination with the vaccine composition sold under the tradename RespiSure at three weeks of age.

TABLE VII

| Source of lymphoid cells | Antigen | Mean cpm($^3$H-thymidine incorporation) | |
|---|---|---|---|
| | | Piglets born to and nursed by vaccinated sows | Piglets born to and nursed by non-vaccinated sows |
| Lymph nodes (BLN) | M.hyopn. | 5,600 | 20,200 |
| Lymph nodes (PLN) | " | 15,100 | 8,600 |
| Spleen | " | 14,700 | 10,100 |
| PBLs | " | 14,500 | 7,200 | n = 12 to 16 piglets

Whereas marked increases in the CMI responses were observed in lymphoid cells from bronchial lymph nodes (BLN) 4 and 7 days post challenge with virulent *M. hyopneumoniae*, CMI responses of splenic, PBLs and BLN lymphocytes were down regulated in that very low responses were observed on days 4 and 7 post infection. An increase in CMI responses in these compartments was observed on day 11 post challenge using conventional techniques. However by this time, BLN lymphocytes from placebo animals challenge-infected in a similar manner also showed high CMI responses.

Although the example provided herein demonstrates this method with a particular *M. hyopneumoniae* vaccine administered to pigs, this invention is not limited thereby. The vaccine composition may contain other Mycoplasma antigens, and other species of Mycoplasma antigens. Additionally, the vaccine composition may contain combinations of Mycoplasma antigens, including antigens from the same species or different species of Mycoplasma.

It is anticipated that this method of the invention can be used to enhance newborn CMI responses to other vaccinal proteins derived from pathogenic microorganisms or viruses, such as feline infectious peritonitis virus, feline immunodeficiency virus, bovine rotavirus, canine parvovirus, Borrelia, and bovine *P. haemolytica*. It is anticipated to be especially useful in any animal species, particularly mammals, including humans, feline, canine and bovine, and in avian species, particularly poultry, including chicken and turkeys.

Numerous modifications and variations of the present invention are included in the above-identified specification and are expected to be obvious to one of skill in the art. Such modifications and alterations to the methods of the present invention are believed to be encompassed in the scope of the claims appended hereto.

What is claimed is:

1. A method for enhancing a cell mediated immune response to *Mycoplasma hyopneumoniae* in a newborn swine comprising the steps of:

a) administering a vaccine composition which comprises an effective immunizing amount of a protective antibody-inducing antigen present in binary ethyleneimine-inactivated *Mycoplasma hyopneumoniae* strain P-5722-3 (ATCC Accession No. 55052.) to a sow prior to the birth of its newborn; and b) subsequently administering an effective amount of said vaccine composition to the newborn after it has ingested the colostrum of the sow.

2. The method according to claim 1 wherein the female animal is administered the vaccine composition prior to breeding.

3. The method according to claim 1 wherein the female animal is administered the vaccine composition during its pregnancy.

4. The method according to claim 3 wherein the female animal is administered the vaccine composition between about 2 weeks and about 6 weeks prior to giving birth.

5. The method according to claim 1 wherein the newborn is first administered an effective amount of the vaccine composition about 3 days to about 3 weeks after birth.

6. The method according to claim 5 wherein the newborn is administered a second effective amount of the vaccine composition about two weeks following the first administration.

* * * * *